United States Patent [19]
Mullin et al.

[11] Patent Number: 5,091,570
[45] Date of Patent: Feb. 25, 1992

[54] METHOD FOR PREPARATION OF DIALKYL TELLURIUM AND DIALKYL SELENIUM

[75] Inventors: John B. Mullin, West Malvern, England; David J. Cole-Hamilton, Boarhills, Scotland; Deodatta V. Shenai-Khatkhate, St. Andrews, Scotland; Paul Webb, Crail, Scotland

[73] Assignee: Secretary of State for Defence in her Britannic Majesty's Gov. of the U.K., London, United Kingdom

[21] Appl. No.: 488,076
[22] PCT Filed: Dec. 2, 1988
[86] PCT No.: PCT/GB88/01065
§ 371 Date: Jul. 31, 1990
§ 102(e) Date: Jul. 31, 1990
[87] PCT Pub. No.: WO89/05292
PCT Pub. Date: Jun. 15, 1989

[30] Foreign Application Priority Data
Dec. 4, 1987 [GB] United Kingdom ............. 8728392

[51] Int. Cl.$^5$ ............................ C07C 395/00
[52] U.S. Cl. .................................. 562/899
[58] Field of Search ......................... 562/899

[56] References Cited
U.S. PATENT DOCUMENTS
1,578,731  3/1926  Hochwalt ............. 562/899
4,946,994  8/1990  Higa .................. 562/899

FOREIGN PATENT DOCUMENTS
243495A1  3/1987  German Democratic Rep. .................. 562/899

OTHER PUBLICATIONS
International Publication WO89/05292, 6/15/89.
Engman et al., "Synthetic Communication", 12(3), pp. 163-165, 1982.
Jones et al., "J. Organomet. Chem.", 255, pp. 61-70, 1983.

Primary Examiner—Paul F. Shaver
Attorney, Agent, or Firm—Nixon & Vanderhye

[57] ABSTRACT

Tellurium and selenium dialkyls are prepared by reacting the corresponding tetrahalide with a Group I metal alkyl.

34 Claims, No Drawings

METHOD FOR PREPARATION OF DIALKYL TELLURIUM AND DIALKYL SELENIUM

This invention relates to a method for the preparation of dialkyl of the Group VI metals tellurium and selenium.

The metals Tellurium and Selenium are of importance in semi-conductor technology, for example in the preparation of the infra red detector material cadmium mercury telluride (CMT) and in light sensing switches respectively.

It is well known that the presence of impurities in semi-conductor materials is extremely undesirable. It is therefore useful to be able to prepare semiconductor materials and chemical precursors used in their manufacture in a high degree of purity. An important series of such chemical precursors is the alkyls of the relevant semiconductor material, which can relatively easily be thermally dissociated to form an epitaxial layer of the material or a layer containing the material. Such alkyls have the additional advantage that they are otherwise relatively stable and may be purified further via the formation of adducts with for example Lewis base adjuvants such as trialkyl or triaryl Group V compounds.

The formation of various addjucts for semiconductor purification is described for example in GB 850955-A, together with a method for preparation of Group II metal alkyls. The preparation of other alkyls can present problems, and in particular the preparation of the Group VI alkyls such as those of tellurium and selenium in a pure state has until now presented great difficulty.

At present methods for preparation of tellurium alkyls are known. Synthetic Communications 12(3), (1982), 163-165 describes a method for preparation of dialkyl ditellurium by reaction of the corresponding lithium alkyl and elemental tellurium in THF with atmospheric oxidation, tellurium dialkyl not being formed. Similarly J. Organometallic Chemistry 255, (1983), 61-70 describes the preparation of mixtures of tellurium dialkyls and ditellurium dialkyls by reaction of the corresponding Grignard reagent RMgCl with tellurium IV chloride. This reaction is believed to result in contamination of the product with RTeCl.

The present invention seeks to overcome or alleviate the problems outlined above by providing a method for the preparation of dialkyls of tellurium and selenium in a substantially more pure state, or at least in a state that facilitates further purification. Other objects and advantages of the present invention will be apparent from the following description.

According to the present invention a method for the preparation of dialkyl tellurium or dialkyl selenium comprises reacting either elemental tellurium or elemental selenium, or a tellurium IV or selenium IV halide with a Group I metal alkyl in a solvent which is or contains at least one $C_4$-$C_{10}$ aliphatic ether, and optionally also contains a liquid alkane.

The reaction is preferably carried out under conditions which exclude atmospheric oxygen, for example under an inert atmosphere eg nitrogen. Oxidation by the atmosphere can result in impurities.

A preferred temperature is below 20° C., especially −40° C. to 0° C. Above room temperature impurities may be formed, such as neohexyl Group I metal alkyls.

The method is suitable for the preparation of all dialkyls, but is especially suitable for the preparation of di-$C_1$-$C_4$ alkyls of tellurium and selenium, which may be straight chain, branched or tertiary alkyls, for example tellurium and selenium dimethyl, diethyl, dipropyl (n- and iso-) or dibutyl (n-, iso- and tert-), especially tellurium dimethyl and di-tert.-butyl.

The Group I metal is preferably lithium, sodium or potassium, especially lithium. Preferred Group I metal alkyls are therefore MeLi and tert.-BuLi.

Preferably the ether is a di- $C_2$-$C_5$ alkyl ether, especially a di-n-alkyl ether. The alkyl groups of the dialkyl or di-n-alkyl ether may be the same or different and a particularly preferred ether is diethyl ether. Whatever ether is/are used, it/they should preferably have a low boiling point.

If an alkane is present it must be liquid at the reaction temperature, and suitable alkanes include n-pentane.

When a halide of the Group VI element is used it is preferably the chloride, eg Te(IV)Cl$_4$ or Se(IV)Cl$_4$.

The reaction is preferably carried out using about stoichiometric quantities of the reactants. Preferably the Group I metal alkyl is dissolved in the alkane, and this solution is added slowly to the element or halide suspended or dissolved in the ether. Following reaction the mixture may be stood at room temperature or refluxed if necessary to ensure completion. The solution of the dialkyl product may be separated from solid residues by filtration. Excess Group I alkyl may be destroyed by adding water. The tellurium or selenium dialkyl may then be isolated by evaporation of the solvent followed by vacuum distillation.

The method of the invention provides dialkyls of tellurium or selenium suitable for use in semiconductor formation, eg in epitaxial deposition. It may however be preferable in some cases to further purify the dialkyls by the known process of secondary adduct formation to produce an adduct with a lower dissociation temperature than that of the dialkyl itself at the pressure of secondary adduct dissociation. Other known further purification methods may be used.

The Group VI dialkyls produced using the method of this invention also constitute a novel product, being in a generally purer form than has been hitherto available using known preparation processes.

The invention will now be described by way of example only. (note: in this patent application the abbreviations Me=methyl, Et=ethyl, Pr=propyl and Bu=butyl are used).

EXAMPLE 1

Synthesis of di-tert-butyl tellurium from elemental tellurium and t-BuLi in Et$_2$O A solution of tert-butyllithium (450 cm$^3$, 1.7 moles dm$^{-3}$) in pentane was added dropwise to an ethereal suspension (300 cm$^3$) of elemental tellurium (90 g, 0.70 g atom) maintained at −40°-0° C. over a period of 5h. An exothermic reaction occurred and the reaction mixture was stirred for 1h after the complete addition, and was then refluxed for 2h. The deep yellow ether-pentane solution of di-tert-butyl tellurium was isolated from excess tellurium and the resulting lithium telluride by filtration. Water was added to destroy any excess tert-butyl lithium. The ether-pentane solution of di-tert-butyl tellurium was separated, dried over anhydrous calcium chloride and, after filtration, diethyl ether and pentane were removed in vacuo. The resulting deep yellow oil was purified by vacuum distillation over calcium hydride. Overall yield=49%.

EXAMPLE 2

Preparation of Di-tert-butyl tellurium from tetrachlorotellurium (IV) and t-BuLi in Et$_2$O A solution of tert-butyllithium (830 cm$^3$, 1.7 moles dm$^{-3}$) in pentane was added dropwise to an ethereal solution of tellurium(IV) chloride (100 g, 0.37 g moles) at 0° C. over 6h. An exothermic reaction occurred and the reaction mixture was stirred for 1h after the complete addition, and was then refluxed for 2h. The pale yellow ether-pentane solution of di-tert-butyl-tellurium was isolated from the resulting lithium chloride by filtration. Water was added to destroy any excess tert-butyl-lithium. The ether pentane solution of di-tert-butyltellurium was separated, dried over anhydrous calcium chloride and after filtration, diethyl ether and pentane were removed in vacuo. The resulting deep yellow oil was purified by vacuum distillation over calcium hydride. Overall yield=62%.

EXAMPLE 3

Synthesis of dimethyltelluride from elemental tellurium and methyllithium in Et$_2$O.

To a grey suspension of elemental tellurium (27.11 g, 0.2124 g atom) in diethyl ether (150 cm$^3$) maintained at temperature between −40°–0° C. was added a pentane solution of methyllithium (140 cm$^3$, 1.5 moles dm$^{-3}$) dropwise over a period of 2h. An exothermic reaction was found to occur. When the addition of methyllithium was complete the reaction mixture was brought to room temperature and was heated under a gentle reflux for a further 2h. The reaction product at this stage consisted of a red supernatant solution and a white amorphous residue. The red supernatant solution was isolated from the white residue by filtration and was then treated with distilled water (50 cm$^3$) to destroy any unreacted methyllithium. The ethereal solution was isolated from the aqueous layer dried over anhydrous calcium chloride, an after filtration, diethyl ether and pentane were removed by fractional distillation at 1 atmos. pressure under dry nitrogen. The dimethyltelluride was distilled at 1 atm (B.P. 83°–84° C.) and the resulting yellow oil was purified by vacuum distillation (overall yield=85%).

We claim:

1. A method for the preparation of dialkyl tellurium or dialkyl selenium comprising reacting either elemental tellurium or elemental selenium, or a tellurium (IV) halide or selenium (IV) halide with a group (I) metal alkyl in a solvent which is or contains at least one C$_4$–C$_{10}$ aliphatic ether.

2. The method according to claim 1 wherein the dialkyl tellurium or selenium is a di- C$_1$ to C$_4$ alkyl.

3. The method according to claim 2 wherein di-tert butyl tellurium is prepared.

4. The method according to claim 3 wherein dimethyl tellurium is prepared.

5. The method according to claim 1 wherein the halide of tellurium (IV) or selenium (IV) is the chloride.

6. The method according to claim 1 or 2 wherein the Group (I) metal is lithium, potassium or sodium.

7. The method according to claim 6 wherein the Group (I) metal is lithium.

8. The method according to claim 6 wherein the Group (I) metal alkyl is lithium, sodium or potassium methyl, ethyl, n-propyl, iso-propyl, n-butyl, iso-butyl or tert-butyl.

9. The method according to claim 8 wherein the group (I) metal alkyl is tert-butyllithium or methyllithium.

10. The method according to claim 1 wherein the solvent is a dialkyl ether.

11. The method according to claim 10 wherein the solvent is diethyl ether.

12. The method according to claim 1 wherein the reaction is carried out under conditions which exclude atmospheric oxygen.

13. The method according to claim 1 wherein the reaction is carried out below 20° C.

14. The method according to claim 13 wherein the reaction is carried out at −40° C. to 0° C.

15. The method according to claim 1 wherein ditert-butyl tellurium is prepared by the reaction of t-BuLi with elemental tellurium at a temperature below 20° C. in a solvent that contains diethyl ether.

16. The method according to claim 1 wherein ditert-butyl tellurium is prepared by the reaction of t-BuLi with tetrachlorotellurium (IV) at a temperature below 20° C. in a solvent that contains diethyl ether.

17. The method according to claim 1 wherein dimethyl tellurium is prepared by the reaction of methyllithium with elemental tellurium at a temperature below 20° C. in a solvent that contains diethyl ether.

18. The method according to claim 1 wherein a liquid alkane is also present during the reaction.

19. The method according to claim 18 wherein the dialkyl tellurium or selenium is a di- C$_1$ to C$_4$ alkyl.

20. The method according to claim 19 wherein di-tert butyl tellurium is prepared.

21. The method according to claim 19 wherein dimethyl tellurium is prepared.

22. The method according to claim 18 wherein the halide of tellurium (IV) or selenium (IV) is the chloride.

23. The method according to claim 18 wherein the Group (I) metal is lithium, potassium or sodium.

24. The method according to claim 23 wherein the group (I) metal is lithium.

25. The method according to claim 23 wherein the Group (I) metal alkyl is lithium, sodium or potassium methyl, ethyl, n-propyl, iso-propyl, n-butyl, iso-butyl or tert-butyl.

26. The method according to claim 25 wherein the Group (I) metal alkyl is tert.-butyllithium or methyllithium.

27. The method according to claim 18 wherein the solvent is a dialkyl ether.

28. The method according to claim 27 wherein the solvent is a diethyl ether.

29. The method according to claim 18 wherein the reaction is carried out under conditions which exclude atmospheric oxygen.

30. The method according to claim 18 wherein the reaction is carried out below 20° C.

31. The method according to claim 30 wherein the reaction is carried out at −40° C. to 0° C.

32. The method according to claim 18 wherein ditert-butyl tellurium is prepared by the reaction of t-BuLi with elemental tellurium at a temperature below 20° C. in a solvent that contains diethyl ether.

33. The method according to claim 19 wherein ditert-butyl tellurium is prepared by the reaction of t-BuLi with tetrachlorotellurium (IV) at a temperature below 20° C. in a solvent that contains diethyl ether.

34. The method according to claim 19 wherein dimethyl tellurium is prepared by the reaction of methyllithium with elemental tellurium at a temperature below 20° C. in a solvent that contains diethyl ether.

* * * * *